US012127924B2

(12) United States Patent
Di Berardino et al.

(10) Patent No.: US 12,127,924 B2
(45) Date of Patent: Oct. 29, 2024

(54) METHOD AND APPARATUS OF MANUFACTURING A MULTILAYER ABSORBING ELEMENT FOR SANITARY ARTICLES

(71) Applicant: TEXOL S.R.L., Alanno (IT)

(72) Inventors: Marino Di Berardino, Roccamontepiano (IT); Fabio Di Berardino, Roccamontepiano (IT)

(73) Assignee: TEXOL S.R.L., Alanno (IT)

( * ) Notice: Subject to any disclaimer, the term of this patent is extended or adjusted under 35 U.S.C. 154(b) by 1228 days.

(21) Appl. No.: 16/757,536

(22) PCT Filed: Nov. 6, 2018

(86) PCT No.: PCT/IB2018/058706
§ 371 (c)(1),
(2) Date: Apr. 20, 2020

(87) PCT Pub. No.: WO2019/092594
PCT Pub. Date: May 16, 2019

(65) Prior Publication Data
US 2021/0186777 A1    Jun. 24, 2021

(30) Foreign Application Priority Data
Nov. 8, 2017    (IT) .......................... 102017000127010

(51) Int. Cl.
*A61F 13/511*    (2006.01)
*A61F 13/15*    (2006.01)
*A61F 13/512*    (2006.01)

(52) U.S. Cl.
CPC .... *A61F 13/5116* (2013.01); *A61F 13/15203* (2013.01); *A61F 13/15699* (2013.01);
(Continued)

(58) Field of Classification Search
CPC ............ A61F 13/5116; A61F 13/15203; A61F 13/15699; A61F 13/15764; A61F 13/51104; A61F 13/5123
See application file for complete search history.

(56) References Cited

U.S. PATENT DOCUMENTS 11,696,856 B2 *    7/2023    Erdem ................ A61F 13/5123
                                                               604/378
2007/0048498 A1    3/2007    Cree
(Continued)

FOREIGN PATENT DOCUMENTS

EP    0235309 A1    9/1987
JP    H05176953 A    7/1993
(Continued)

OTHER PUBLICATIONS

International Search Report and Written Opinion for Corresponding International Application No. PCT/IB2018/058706 (8 Pages) (Jan. 10, 2019).
(Continued)

*Primary Examiner* — Ariana Zimbouski
(74) *Attorney, Agent, or Firm* — LUCAS & MERCANTI, LLP (57) ABSTRACT

An apparatus for making a multilayer absorbent element apt to be incorporated in a sanitary article is provided. The apparatus has an embossing roller bearing a plurality of protruding elements, a pierced roller bearing a plurality of protruding elements and cavities, and a unit of cohesion and drilling. The configuration of the apparatus is such that, after a first layer of sheet material is deformed by the embossing roll and the perforated roller continues to slide on the pierced roller, a second layer of sheet material is superimposed. The first and second layer of sheet material are then carried to the joining and piercing unit in which, at the intermediate zones of the first layer, it forms a plurality of holes passing through the first and second layer and joins them near or at the plurality of holes.

24 Claims, 7 Drawing Sheets (52) U.S. Cl.
CPC .. *A61F 13/15764* (2013.01); *A61F 13/51104* (2013.01); *A61F 13/5123* (2013.01); *A61F 2013/15414* (2013.01); *A61F 2013/15869* (2013.01); *A61F 2013/15878* (2013.01); *A61F 2013/51165* (2013.01)

(56) References Cited

U.S. PATENT DOCUMENTS

| | | |
|---|---|---|
| 2013/0197462 A1 | 8/2013 | Abuto et al. |
| 2018/0177643 A1* | 6/2018 | Hao .................. B32B 7/04 |

FOREIGN PATENT DOCUMENTS

| | | |
|---|---|---|
| JP | 2008073396 A | 4/2008 |
| JP | 2009268559 A | 11/2009 |
| JP | 2017093731 A | 6/2017 |
| WO | 03048436 A2 | 6/2003 |
| WO | 2015098373 A1 | 7/2015 |

OTHER PUBLICATIONS

International Preliminary Report On Patentability For Corresponding International Application No. PCT/IB2018/058706 (19 Pages) (Jan. 30, 2020).

\* cited by examiner

METHOD AND APPARATUS OF MANUFACTURING A MULTILAYER ABSORBING ELEMENT FOR SANITARY ARTICLES

CROSS-REFERENCE TO RELATED APPLICATIONS

This application is a 371 of PCT/IB2018/058706, filed Nov. 6, 2018, which claims the benefit of Italian Patent Application No. 102017000127010, filed Nov. 8, 2017.

TECHNICAL FIELD OF THE INVENTION

The present invention refers to a multilayer absorbent element for sanitary articles, in particular a so-called "topsheet".

The invention also refers to a method and an apparatus for manufacturing such element.

BACKGROUND

Numerous sanitary articles with absorbent function are present on the market, such as diapers for children, products for senile and light incontinence and feminine sanitary pads.

Generally, such articles comprise an absorbent core and a multilayer element, that is absorbent too. The latter, commonly denoted as a "topsheet", is interposed between the user's skin and the absorbent core during use.

The function of the topsheet is to collect the flow of organic fluid, for example urine or menstrual blood, and transfer it to the underlying absorbent core so as to provide the user with a feeling of comfort and dryness. Therefore, the topsheets must be soft, of nice aspect to the user and have good absorption characteristics.

Generally, the structure of a topsheet is formed by two overlapping layers of sheet material. The first layer acts as a receptor and is, in use, in contact with the user's skin; therefore, such first layer must be soft and with a slight tendency to "lint", that is the release of fibrous or loamy residues. The second layer, interposed between the upper layer and the absorbent core, must be denser and provided with greater capillary power with respect to the first layer, so as to dry the latter by draining and transferring the organic fluid to the absorbent core.

In known topsheets, this structure is obtained by coupling two layers of sheet material of different type of "non-woven fabric" (NWF), in order to guarantee that each of the two layer has the abovementioned respective characteristics. The NWF layers can be pierced, thus facilitating the drainage of the liquid from the first upper layer to the lower second layer. Furthermore, in order to make the topsheet particularly soft, a "concave-convex" structure is conferred to it, characterized by an alternation of protrusions and depressions.

The abovementioned shaped structure is commonly obtained by means of a manufacturing process which employs, for the second topsheet layer, NWF formed by heat-retractable fibers ("self-crimping fibers"), i. e. capable of autonomously contracting with heat. The two NWF layers are initially joined, for example by ultrasound, in some contact points. The layers of NWF thus coupled are then subjected to a heat treatment which activates the contraction of the fibers present in the NWF which constitutes the second layer of the topsheet. This contraction induces the formation of protrusions and depressions on both the layers.

The process just described, and the resulting product, however, shows some drawbacks.

First of all, the shaping of the topsheet makes its adhesion to the absorbent core more difficult and less reliable.

Moreover, said shaping does not allow to optimize the storage of the topsheet in coils or in packaging stacks, also because, in these conditions, the integrity of the conferred shaping cannot be guaranteed.

A further drawback consists then in the need to use heat-retractable fibers for the second layer of NWF, because this impacts negatively on the production process in terms of costs, complexity and time necessary for the manufacturing operations.

SUMMARY OF THE INVENTION

The technical problem posed and solved by the present invention is therefore that of providing a multilayer absorbing element and a related manufacturing method and apparatus which allow to overcome the abovementioned drawbacks with reference to the prior art.

This problem is solved by a manufacturing method according to claim 1 and a related apparatus according to claim 10.

The invention also provides a multilayer absorbent element according to claim 21.

Preferred features of the present invention are the subject of the dependent claims.

The invention provides some relevant advantages. The main advantage lies in the fact that the absorbent element has an improved structure, in which the second layer, being devoid of protrusions or depressions—and in particular flat and/or substantially flat—guarantees a better adherence to the absorbent core, or possibly to other components of the sanitary article. In addition, the structure of the absorbent element allows a better preservation of the characteristics of the material even if the latter is subjected to compression or, in general, stored in the form of stacks or coils.

In a preferred embodiment, the absorbent element can be added with pigments suitable for obtaining a "masking" effect. Such characteristic is appreciated especially in the case of coloured organic fluids, such as urine or menstrual blood, and consists in having an area of the stain of reduced surface and in masking from sight the colour of the fluid absorbed by the different elements of the sanitary article.

In one embodiment, the absorbent element can also perform the function of Acquisition Distribution Layer (ADL), that is an element which accelerates the absorption and distribution of the organic fluid to the other components, in particular to the absorbent core, of the sanitary article. In this way, it is possible to make the manufacturing process of the entire sanitary article simpler, faster and cheaper.

Furthermore, the multilayer element of the invention may have better capacity of absorbency and guarantee the dryness of the sanitary article in which it is incorporated, thus improving the user's comfort of use.

In addition, the manufacturing method according to the present invention allows to reduce the production costs. In fact, this method is simple and quick and moreover requires the use of less expensive raw materials. In fact, the need to use a NWF with heat-retractable fibers for the second layer of the absorbent element is eliminated.

Other advantages, features and methods of use of the present invention will be apparent from the following detailed description of some embodiments, presented by way of a non-limiting example.

BRIEF DESCRIPTION OF THE FIGURES

Reference will be made to the figures of the attached drawings, wherein:

FIG. 1*bis* shows an exemplary schematic cross-sectional view of an absorbent element according to a preferred embodiment of the present invention;

The thicknesses and the profiles shown in the above figures are to be understood as examples, they can be magnified and are not necessarily shown in proportion.

DETAILED DESCRIPTION OF PREFERRED EMBODIMENTS

Hereinafter various embodiments and variants of the invention will be described, with reference to the above figures.

Similar components are denoted in different figures with the same numerical reference.

In the following detailed description, embodiments and further variants with respect to embodiments and variants already disclosed in the description itself will be illustrated only with regard to the differences with what already stated.

Moreover, the various embodiments and variants described below are susceptible of being used in combination, where consistent.

Figure 1:
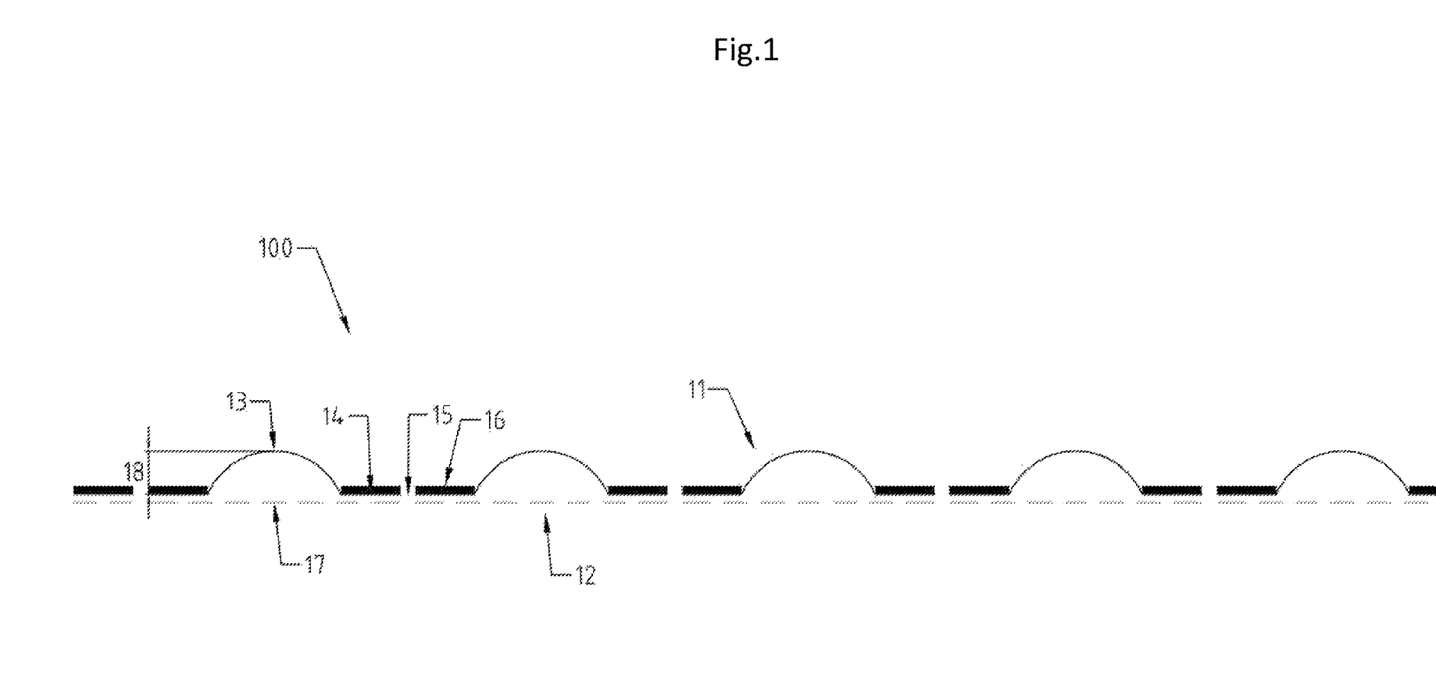
FIG. 1 shows an exemplary schematic cross-sectional view of an absorbent element according to a preferred embodiment of the present invention.

With reference initially to FIG. 1, an absorbent element, and in particular a so-called "topsheet", according to a preferred embodiment of the invention is overall denoted by 100. Such topsheet is suitable to be incorporated in sanitary articles, such as, for example, baby diapers, incontinence products or sanitary pads.

In particular, the topsheet 100 comprises a first layer of sheet material 11 and a second layer of sheet material 12. Such first and/or second layer 11 and 12 can be a laminated material.

The first layer 11, in the present application, during use is in contact with the user's body. It has a structure based on an alternation of protrusions 13 and contractions, depressions, valleys or recesses, that are intermediate zones 14 without said protrusions 13. In the present example, the intermediate zones 14 are substantially flat or planar.

The second layer of sheet material 12 is substantially free of depressions or protrusions, and in particular substantially flat or planar.

In the present embodiment, the protrusions 13 on the first layer 11 can have each a round shape and/or a substantially circular geometry in plan view. In the embodiment shown in FIG. 1, said protrusions 13 have a cylindrical geometry.

Possible embodiments can provide the presence of protrusions 13 with a hemi-spherical geometry. In an exemplary implementation, the base diameter of the protrusions 13 is about 2 mm.

The first and second layers 11 and 12 are superimposed one to the other and are coupled at the intermediate zones 14 of the first layer 11. At these intermediate zones 14, there are a plurality of holes 15 passing between the first layer 11 and the second layer 12, which help to direct the flow of organic fluid to other elements of the sanitary article, in particular towards an absorbent core. In the proximity of each hole 15, the first layer 11 and the second layer 12 are joined to each other, preferably along the perimeter which defines each hole 15.

The drainage of the biological fluid from the first layer 11 to the second layer 12 is facilitated by the presence of a deposition of a surfactant agent 16, which has the function of an hydrophilizing agent. Said surfactant agent 16 is shown in black in FIG. 1. Advantageously, it is deposited on the first layer 11, preferably only on it and not on the second layer 12. In particular, the agent 16 is present in proximity of, or at, walls of the holes 15 or portions of the first layer 11 which are lateral or circumscribed with respect to the same holes, while the remaining areas of the first layer 11 are left substantially hydrophobic or neutral. In this way, a surface tension gradient is realized, both on the first layer 11 and between the latter and the second layer 12, which helps to draw the biological fluid towards the holes 15.

According to embodiment variants, the surfactant agent 16 is also applied onto the protrusions 13, as their total or partial coating.

In one embodiment, the surfactant agent can be applied as "coating" on one or both sides of the layer 11.

In particular, also in this case said agent can be applied further, or only, on the walls of the holes.

A surfactant agent selected from one of those commercially available for hygienic applications can be used. For example, Silastol PST-N® from Schill & Seilacher company in concentrations from 0.3% to 0.6% by weight.

Figure 2:
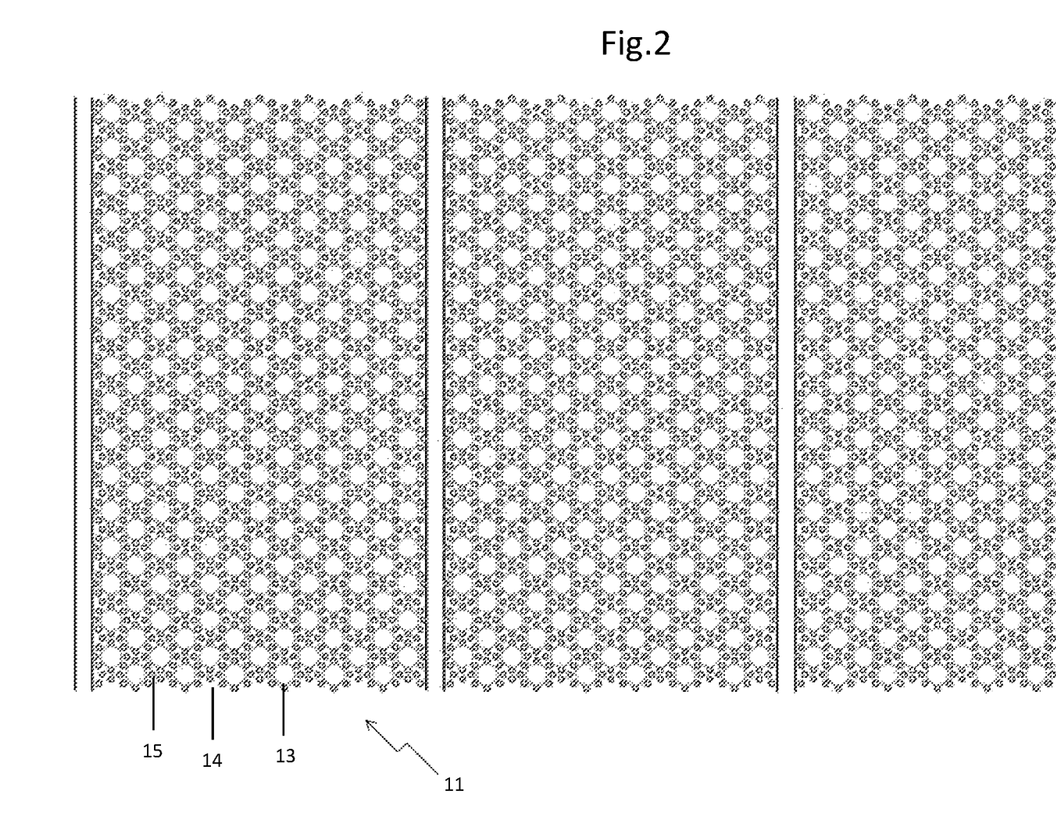
FIG. 2 shows an exemplary schematic top view of an absorbent element according to a preferred embodiment of the present invention.

FIG. 2 shows an exemplary schematic top view of a preferred embodiment of the topsheet. In that Figure it is visible how the first layer 11 presents an alternation of protrusions 13 and intermediate zones 14, at which the holes 15 passing through the first layer 11 and second layer 12 are made.

Preferably, the first layer of sheet material 11 is made of non-woven fabric (NWF).

Preferred characteristics of such NWF are softness and absence of release of fibers.

Furthermore, it is preferable that the NWF is composed by fibers which make it easily joinable with the second layer of sheet material 12.

A NWF suitable for the present application is composed by thermoplastic fibers, which are composed by thermoplastic polymers comprising polyolefins such as polyethylene and polypropylene, polyesters, copolyesters, polyvinyl acetate, polyamides, copolyamides, polystyrene, polyurethanes, and vinyl chloride/vinyl acetate copolymers.

The thermoplastic fibers may be composed by a single polymer (single-component fibers) or may be composed by more than one polymer (e.g. two-component fibers).

The two-component fibers can be composed by a "core" fiber surrounded by a thermoplastic "sheath" composed by a second polymer. The polymer of the "sheath" melts at a lower temperature than the core. As a result, the two-component fibers establish a bond among the fibers due to the melting of the polymer on the sheath, after adequate heat treatment. The resistance characteristics of the core polymer are maintained.

Two-component fibers useful in the present development are those constituted by fibers having the following combinations of sheath/core polymers: polyethylene/polypropylene, polyethylvinylacetate/polypropylene, polyethylene/polyester, polypropylene/polyester, copolyester/polyester.

The two-component fibers can be either concentric or eccentric. Eccentricity is related to section of the bicomponent fiber and depends on how the sheath is centered or not around the core section.

The length of the fibers may vary depending on the properties of the fibers and the manufacturing method of the NWF. Typically, the fibers of the present development have a length of 0.3-7.5 cm, preferably 0.4-3.0 cm. The diameter of the fibers is generally expressed in deniers (grams per 9.000 m of fiber) or in decitex (grams per 10.000 m of fiber). For the present development, the fibers have a decitex in the range of <1 decitex (e.g. 0.4 decitex) up to about 20 decitex.

TNT is generally bonded in order to acquire sufficient integrity and resistance. The technologies widely used for this purpose are: chemical bonding and thermal bonding, by merging part of the web. In the latter case, the fibers can be compressed in separate points that can constitute a significant part of the NWF area. In particular, for structures where it is desired to maintain a low density of the material it is useful to apply the "air-through bonding". In this case, part of the fibers (for example the coat of the two-component fibers) are melted by the use of hot air passing through the web. As the web cools, the partially fused fibers bond with each other at the points where they came into contact.

In some embodiments of the present development, the NWF used can be an airthrough bonded, a carded thermobonded, spunbonded, or spunbond-meltblown-spunbond. The weight of the NWF can be varied according to specific needs. In general, TNWF can be used with weights of 6-150 grams/m$^2$ (gsm) and more preferably 8-20 gsm. The weights are intended to be measured in according to ASTM D3776.

In summary, the total thickness of the first layer can vary from 350 to 1.000 microns and more preferably from 500 to 800 microns. The thicknesses are intended to be measured in accordance with EDANA 30.5-99.

Some examples of manufacturing technologies to manufacture a NWF having similar characteristics are: carded air-through bonded, spunbonded, spunlaced. Finally, the TNT fibers of the first layer 11 may contain additives, in particular pigments, to make them opaque, white or coloured.

The second layer of sheet material 12 preferably is constituted by a plastic film, still more preferably of an olefin or polyolefin film. Said layer could also be elastic. It is also preferable that said second layer of sheet material 12 has a plurality of additional apertures, or holes, 17, shown in FIG. 1, which allow the biological fluid to flow towards the other elements of the absorbent article. To the second layer of sheet material 12 pigments can be added, for example titanium dioxide, to reduce, at the sight, the size of the stain formed by the biological fluid absorbed and to mask its colour.

The holes 15 passing between the first layer 11 and the second layer 12 have a preferably tapered shape, in particular conical; alternatively, such holes 15, as shown in FIG. 1, may have cylindrical geometry. Indicatively, said holes 15 have a diameter of the order of 0.5 mm.

The openings 17 on the second layer 12 have preferably a conical, or alternatively, a cylindrical geometry.

The holes 15 passing between the first 11 and the second layer 12 and/or the openings 17 on the second layer 12 may have different dimensions and/or orientation to each other.

The arrangement and shape of the openings (round, rhomboidal, elliptical, or other) can be customized to guarantee the most suitable solution for specific application needs.

According to a variant embodiment, the position of the first and second layers can be reversed, for example with the second layer provided for contact with the skin of the subject.

Some possible variations of realization provide for the configuration of the topsheet 100 in order to make it also act as "Acquisition Distribution Layer". This can be done by inverting the layers of sheet material 11 and 12 and properly selecting the NWF, or by dimensioning the plastic film which constitutes the second layer 12 in order to have a thickness and mechanical characteristics suitable to make it work as ADL.

According to a different embodiment shown in FIG. 1bis, the holes 15 may be provided only onto the first or second layer. Advantageously, they are provided only on the layer which, during use, is arranged above/in proximity to the subject. In the example of FIG. 1bis, the holes are present only on the first layer 11.

The absorbent element 100 may also constitute a component of a multilayer structure. For example, it may be associated with a third layer of non-woven fabric.

Figure 3:
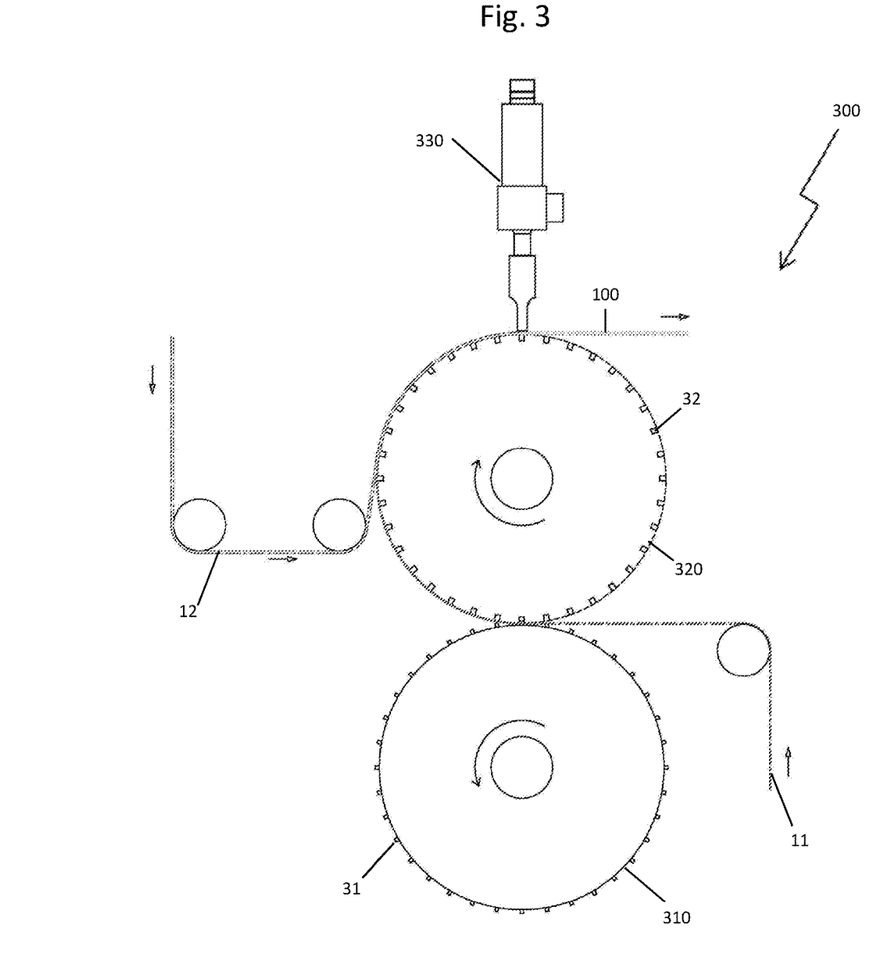
FIG. 3 shows an exemplary schematic representation in a side view of a first preferred embodiment of an apparatus for manufacturing the absorbent element of FIG. 1 or 2.

With reference to FIG. 3, a manufacturing apparatus of the topsheet 100 above described is overall denoted by 300.

The sheet materials which composed the first layer 11 and the second layer 12 mentioned above are fed to the apparatus 300. For the sake of simplicity, these materials are here denoted with the same numerical reference of the layer that they are going to realize. This feeding occurs by known means, for example return and/or feed rollers, schematically shown in the figure, which will not be further described.

The apparatus 300 realizes the topsheet 100 mainly through a sequence of embossing, coupling, joining and piercing phases of the sheet materials.

In particular, the apparatus 300 comprises a rotating embossing roller 310 having a plurality of first protruding elements 31 and configured to be engaged, in use, by the first sheet material 11.

The embossing roller 310 cooperates in rotation with a counter-roller, in particular a pierced roller 320 coupled to it according to opposite rotation directions, as shown in the figure. The pierced roller 320 comprises a plurality of cavities 32, each suitable for receiving a respective protruding element 31 of the embossing roller 310 during a rotation in phase of the rollers themselves. The pierced roller 320 preferably also comprises a second plurality of protruding elements 33, the latter better visible in FIG. 6.

The configuration is such that the first protruding elements 31 cooperate with the cavities 32 to deform the material 11 by embossing. In particular, during the relative rotation a protruding element 31 engages a cavity 32 with interposition of the material 11, realizing one of the protrusions 13 on the latter material 11.

The pierced roller 320 is also fed with the second material 12 which is superimposed on the first material 11 downstream of the deformation of the latter.

In addition, the apparatus 300 advantageously comprises a joining and piercing unit 330, arranged downstream of the roller portion on which the overlapping of the two materials occurs. In particular, in the present example the unit 330 is in a diametrically opposite position with respect to the roller portion at which the engagement and piercing of the first material 11 take place.

The unit 330, cooperating with the protruding elements 33 on the pierced roller 320, realizes a plurality of through holes 15 which pass through the first material 11 and the second material 12 at the intermediate zones 14, that are substantially free of protrusions 13. The same unit 300 then joins, in proximity of the holes 15, the first material 11 and the second material 12. Preferably, the joining occurs along the perimeter defining the holes 15.

Preferably, the joining and piercing unit 330 uses an ultrasonic technology; alternatively, said unit 330 can join the first material 11 and the second material 12 by thermal or mechanical action, for example by the selective application of pressure and depression.

Ultrasounds allow to pierce the material at a higher speed, ensuring a more productive use of production lines.

In a variant embodiment, the unit 330 performs just a joining of the two materials 11 and 12, while the piercing is performed only on the first or second layer, advantageously upstream of said joining.

Figure 4:
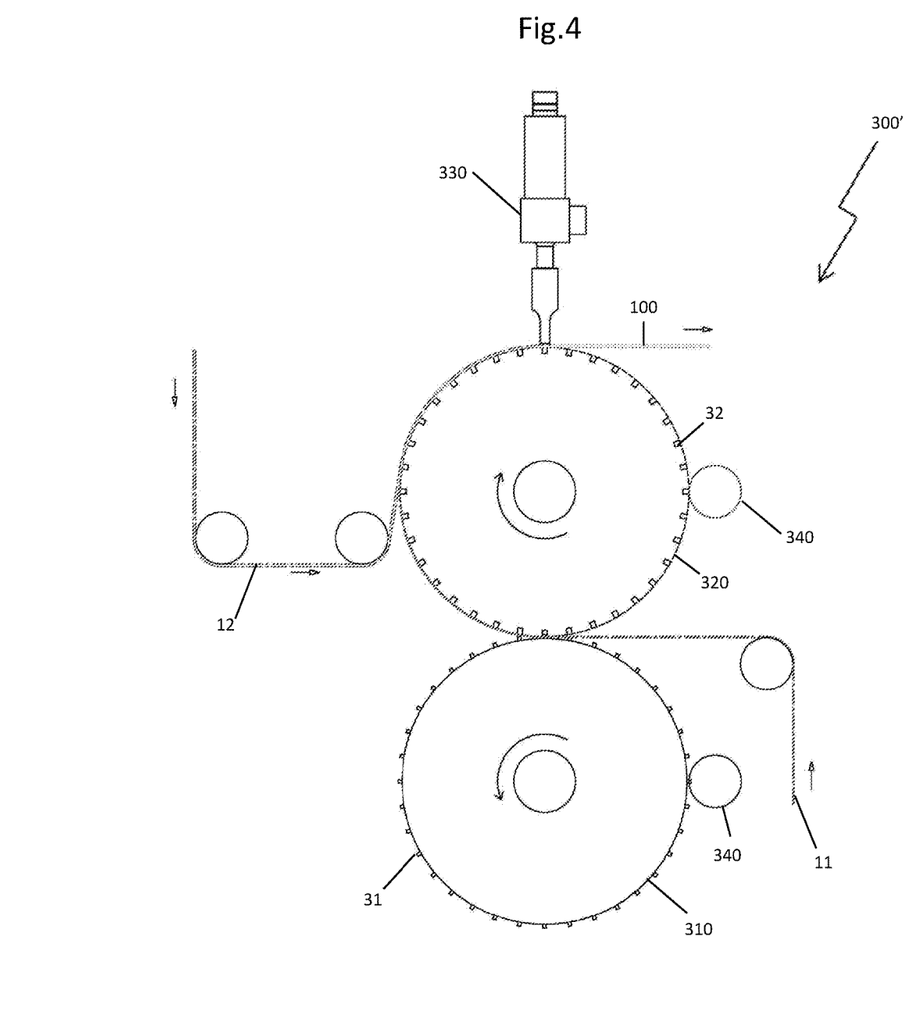
FIG. 4 shows an exemplary schematic representation in lateral view of another preferred embodiment of an apparatus for manufacturing the absorbent element of FIG. 1 or 2.

In an alternative embodiment, shown in FIG. 4, the manufacturing apparatus 300' comprises one or more kiss rollers 340, coupled in rotation to the embossing roller 310 and/or to the pierced roller 320.

The kiss rollers 340 draw on the surfactant agent 16, for example from a tank or tub, and transfer the latter to the surface of the embossing roller 310 and/or of the pierced roller 320 with which they cooperate. Hence, by the physical contact with the embossing roller 310 and the pierced roller 320, the surfactant agent 16 is transferred to the material 11.

In another variant embodiment, the surfactant agent can be applied by means of kiss roll or equivalent means also to the second material.

Moreover, the arrangement of the application means of the surfactant agent can be such that to allow a selective application only at selected areas, for example at or in proximity of the walls of the holes.

In possible alternative embodiments of apparatus 300, no one kiss roller 340 is present. In this case, the surfactant agent 16 may already be present in the first material 11, for example applied to the fibers that constitute the NWF, and/or the surfactant agent 16 may have been applied to the second material 12, for example added in a mixture to the resins of the plastic film and being present on the surface of the film after a migration.

In general terms, the shape of the cavities obtained in the first material 11 is adjusted by selecting the shape of the first protruding elements 31 on the embossing roller 310 and/or the cavities 32 on the pierced roller 320 and/or by their mutual distance and arrangement.

Figure 5:
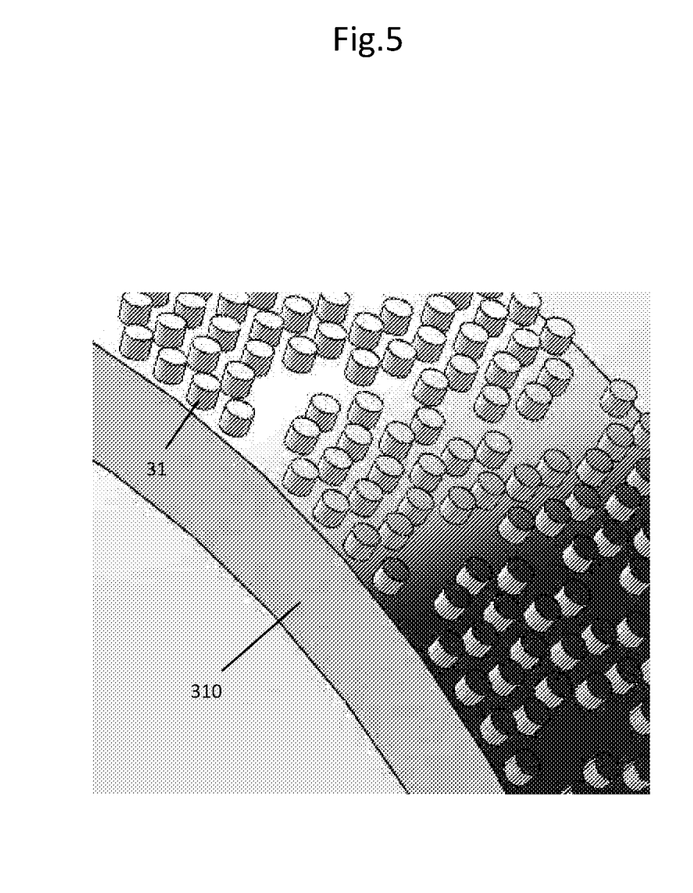
FIG. 5 shows a schematic perspective view of a portion of an embossing roller of the apparatus of FIG. 3 or 4, according to a preferred embodiment thereof.

In a preferred embodiment, shown in FIG. 5, the first protruding elements 31 of the embossing roller 310 have cylindrical geometry. In possible embodiment variants, the geometry of these protruding elements 31 is hemi-spherical. In an exemplary implementation, the diameter of the first protruding elements is about 2 mm.

Figure 6:
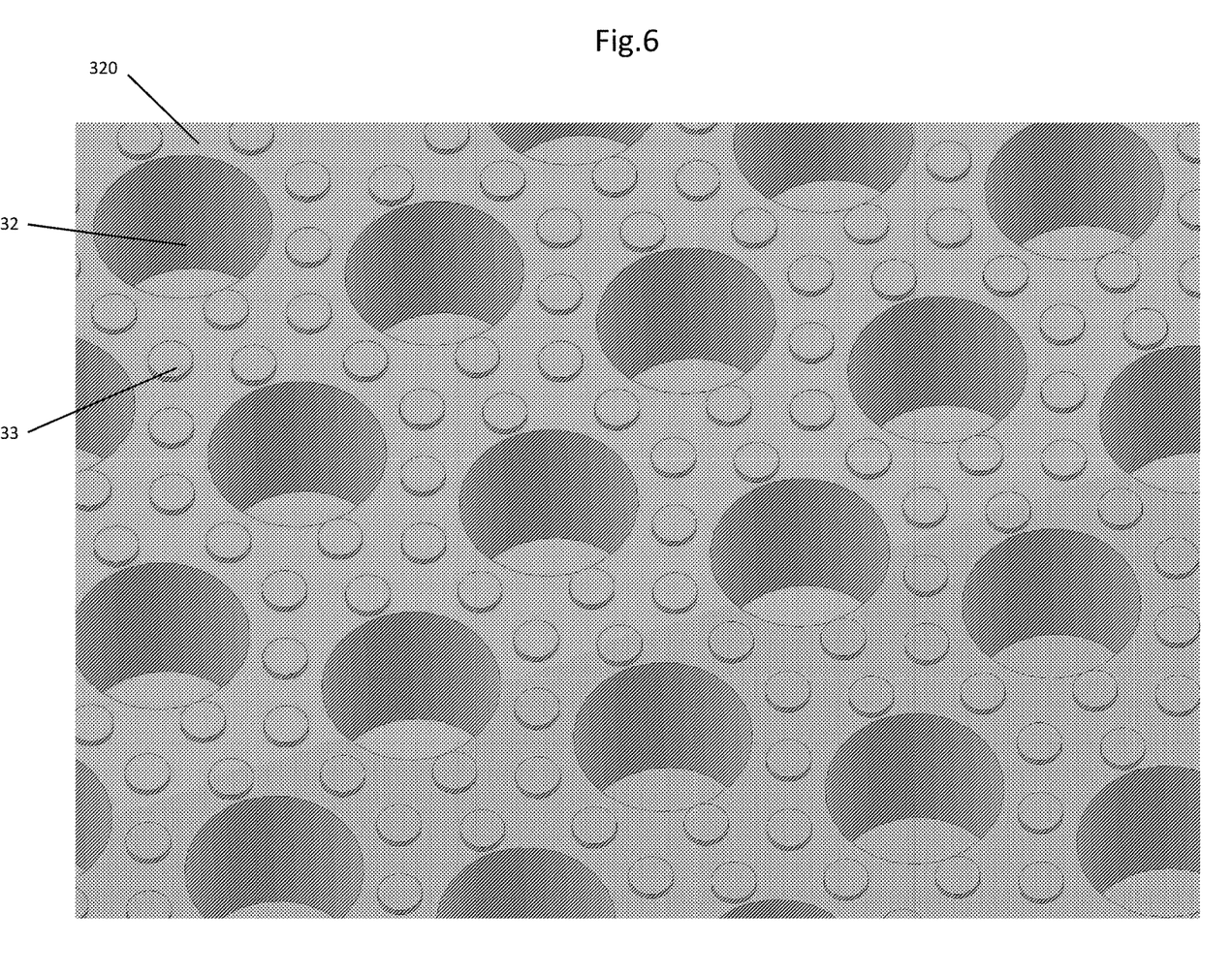
FIG. 6 shows an exemplary schematic perspective top view of a portion of a pierced roller of the apparatus of FIG. 3 or 4, according to a preferred embodiment thereof.

In a preferred embodiment, shown in FIG. 6, the cavities 32 of the pierced roller 320 have a cylindrical geometry. Alternatively, such cavities may have hemi-spherical geometry. Similarly to the first protruding elements 31 with which they cooperate, the cavities 32, in an implementation example, have a diameter of about 2 mm.

Preferably, the second protruding elements 33 on the pierced roller 320, which give rise to the through holes 15, have a tapered profile, in particular cylindrical or frusto-conical. Alternatively, these protruding elements 33 may have cylindrical geometry, as shown in FIG. 6. In general, the diameter of said second protruding elements is about 0.5 mm.

Depending on the specific applications, the described absorbent element can be used by using the first layer of sheet material 11 as top layer and the second layer of sheet material 12 as bottom element, or vice versa.

The present invention has been so far described with reference to preferred embodiments. It is to be understood that other embodiments which belong to the same inventive core may exist, as defined by the scope of the protection of the claims set forth below.

The invention claimed is:

1. A method for manufacturing a multilayer absorbent element for organic fluids capable of being incorporated into a sanitary article, comprising:
    deforming a first layer of sheet material by embossing, to obtain in it a plurality of protrusions alternating with a plurality of intermediate zones without said protrusions and substantially planar;
    overlapping onto said first layer of sheet material a second layer of sheet material;
    making a plurality of through holes on said first layer of sheet material and on said second layer of sheet material, at said intermediate zones of said first layer;
    joining together said first layer and said second layer of sheet material in proximity of, or at, the holes of said plurality;
    wherein said first layer of sheet material is a non-woven fabric (NWF) and said second layer of sheet material is a plastic film,
    wherein a step of application of a hydrophilic onto said first layer is provided, which hydrophilic agent is applied in proximity of, or at, walls of through holes of said plurality, which hydrophilic agent is a surfactant agent, and
    wherein said joining step provides a joining between the first layer of sheet material and the second layer of sheet material performed along the perimeter of each through hole of said plurality.

2. The manufacturing method according to claim 1, wherein said steps of making through holes and joining are performed together in a same unit.

3. The manufacturing method according to claim 1, wherein said joining step is performed by means of a modality selected from the group consisting of: ultrasound application, heat application and pressure application.

4. The manufacturing method according to claim 1, wherein said embossing step is performed by means of a pair of rollers coupled in rotation.

5. The manufacturing method according to claim 1, wherein said second layer of sheet material has a further plurality of holes or openings.

6. The manufacturing method according to claim 1, wherein said first layer of sheet material and/or said second layer of sheet material is a laminated material.

7. The manufacturing method according to claim 1, wherein said through holes are made in conjunction onto said first layer of sheet material and onto said second layer of sheet material.

8. A multi-layer absorbent element for organic fluids, capable of being incorporated into a sanitary article, which absorbent element comprises:
    a first layer of a sheet material, having a plurality of protrusions and a plurality of intermediate zones without such protrusions, wherein said first layer of sheet material is a non-woven fabric (NWF); and a second layer of a sheet material, superimposed on said first layer, which second layer of sheet material is a plastic film;

wherein at, or in proximity of, said intermediate zones, said first layer of sheet material and/or said second layer of sheet material have a plurality of through holes, wherein in proximity of, or at, said through holes, said first layer and second layer are joined to each other, wherein in proximity of, or at, said through holes, there is a surfactant agent, applied onto said first layer, and wherein the joining between the first layer of sheet material and the second layer of sheet material is performed along the perimeter of each through hole of said plurality.

9. The multi-layer absorbent element according to claim 8, wherein each of said through holes has a substantially conical or cylindrical profile.

10. The multi-layer absorbent element according to claim 8, wherein each of said protrusions has a substantially cylindrical or hemi-spherical profile.

11. The multi-layer absorbent element according to claim 10, wherein each protrusion has a diameter of about 2 mm.

12. The multi-layer absorbent element according to claim 8, wherein said first layer of sheet material has a thickness of about 350-1.000 microns and/or a grammage of 6-150 grams/m$^2$ (gsm).

13. The multi-layer absorbent element according to claim 8, wherein said first layer of sheet material includes fillers to make it opaque and/or coloured.

14. The multi-layer absorbent element according to claim 8, wherein said second layer of sheet material is substantially planar.

15. The multi-layer absorbent element according to claim 8, wherein said second layer of sheet material has an olefinic or polyolefinic film.

16. The multi-layer absorbent element according to claim 8, wherein said second layer of sheet material has a thickness of 0.3-6. mm.

17. The multi-layer absorbent element according to claim 8, wherein said second layer of sheet material includes substances capable of masking the amount and the colour of the absorbed organic fluids, a substance of said substances optionally being titanium dioxide.

18. The multi-layer absorbent element according to claim 8, wherein said second layer of sheet material has a plurality of openings.

19. The multi-layer absorbent element according to claim 18, wherein each of said openings has a substantially cylindrical profile.

20. The multi-layer absorbent element according to claim 18, wherein each of said openings has a substantially tapered profile, said tapered profile optionally being conical or frusto-conical.

21. The multi-layer absorbent element according to claim 19, wherein each of said openings has a diameter of about 0.5 mm.

22. The multi-layer absorbent element according to claim 20, wherein each of said openings has a maximum diameter of about 0.5 mm.

23. The multi-layer absorbent element according to claim 8, wherein said through holes and/or said openings have different dimensions and/or different orientation.

24. A sanitary article comprising the multilayer absorbent element according to claim 8.

* * * * *